United States Patent [19]
Phillips et al.

[11] Patent Number: 5,863,559
[45] Date of Patent: Jan. 26, 1999

[54] ORAL DOSAGE FORM FOR TREATING MIGRAINE

[75] Inventors: Anthony John Phillips, Ware, Great Britain; Ian Keith Winterborn, Mississauga, Canada; John Malcolm Padfield, Uxbridge, Great Britain

[73] Assignee: Glaxo Group Limited, Greenford, England

[21] Appl. No.: 381,422

[22] PCT Filed: Mar. 2, 1992

[86] PCT No.: PCT/EP92/00460

§ 371 Date: Aug. 31, 1993

§ 102(e) Date: Aug. 31, 1993

[87] PCT Pub. No.: WO92/15295

PCT Pub. Date: Sep. 17, 1992

Related U.S. Application Data

[63] Continuation of Ser. No. 107,847, Aug. 31, 1993, abandoned.

[30] Foreign Application Priority Data

Mar. 8, 1991 [GB] United Kingdom ................... 9104890

[51] Int. Cl.$^6$ ........................................................ A61K 9/36
[52] U.S. Cl. ........................ 424/480; 424/464; 424/465; 424/475
[58] Field of Search ................................. 424/464, 465, 424/475, 480

[56] References Cited

U.S. PATENT DOCUMENTS

| | | | |
|---|---|---|---|
| 4,816,470 | 3/1989 | Dowle et al. | 514/415 |
| 4,894,387 | 1/1990 | Butina et al. | 514/415 |
| 5,037,845 | 8/1991 | Oxford | 514/415 |

FOREIGN PATENT DOCUMENTS

| | | |
|---|---|---|
| A-0147107 | 7/1985 | European Pat. Off. . |
| 0 433 043 | 6/1991 | European Pat. Off. . |
| 2 124 210 | 2/1984 | United Kingdom . |
| A-2162522 | 2/1986 | United Kingdom . |

OTHER PUBLICATIONS

Remingtons pharmaceutical Sciences (17th edition) pp. 1605–1606 (1985).

The Bantam Medical Dictionary by John Wiley & Sons pp. 196, 320 (1990).

King; Remington's Pharmaceutical Sciences; Fifteenth Edition, 1975; 89; pp. 1576–1577.

Wilkinson; Cephalalgia, vol. 3, 1983; pp. 61–67.

Volans; Chemical Pharmacokinetics 3: 1978; pp. 313–318.

Patten; J. Neurol (1991); 238: S62–S65.

Hussey; Clin. Pharm. Ther. (1991), 49(2), Abs. pp. 1–46.

*Primary Examiner*—Jyothsna Venkat
*Attorney, Agent, or Firm*—Bacon & Thomas

[57] ABSTRACT

A pharmaceutical composition for oral adminstration comprising a film-coated solid dosage form including 3-[2-(dimethylamino)ethyl]-N-methyl-1H-indole-5-methanesulphonamide or a pharmaceutically acceptable salt or solvate thereof as active ingredient.

The film-coated solid dosage forms are of use in the treatment of conditions associated with cephalic pain, in particular migraine.

6 Claims, No Drawings

ORAL DOSAGE FORM FOR TREATING MIGRAINE

This application is a Continuation of application Ser. No. 08/107,847, filed Aug. 31, 1993, now abandoned.

The present invention relates to a pharmaceutical composition containing as active ingredient 3-[2-(dimethylamino)ethyl]-N-methyl-1H-indole-5-methanesulphonamide, in particular a composition for oral administration.

3-[2-(dimethylamino)ethyl]-N-methyl-1H-indole-5-methanesulphonamide, which may be represented by the formula (I)

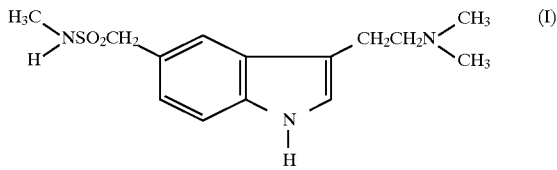

and its physiologically acceptable salts and solvates are disclosed in UK Patent Specification No. 2162522. The compound of formula (I) exhibits selective vasoconstrictor activity and is useful in the treatment of migraine.

Oral administration constitutes the generally preferred route for administration of pharmaceuticals since this route is particularly convenient and acceptable to patients. Unfortunately oral compositions may be associated with certain disadvantages in the treatment of conditions associated with cephalic pain. For example, such conditions, particularly migraine are associated with gastrointestinal dysfunction in the form of delayed gastric emptying. This leads to both a delay and an impairment of drug absorption and it is generally accepted that oral formulations of drugs for the treatment of such conditions should be administered in the form of a liquid preparation.

Numerous clinical studies have demonstrated the effectiveness of the compound of formula (I) in migraineurs. Hitherto, the drug has always been administered either by parenteral injection or in the form of a dispersible tablet which is dispersed in drinking water prior to oral administration. This mode of oral administration was believed to minimise the potential problems associated with gastrointestinal dysfunction in migraineurs.

However, it has been found that the compound of formula (I) has a particularly unpleasant taste. When the compound of formula (I) is administered orally this unpleasant taste may exacerbate the nausea and vomiting associated with migraine.

The present invention provides a particularly advantageous formulation suitable for oral administration of the compound of formula (I).

There is thus provided according to the invention a pharmaceutical composition for oral administration comprising a film-coated solid dosage form including 3-[2-(dimethylamino)ethyl]- N-methyl-1H-indole-5-methanesulphonamide or a pharmaceutically acceptable salt or solvate thereof as active ingredient.

As used herein the term "film-coated solid dosage form" means a solid core comprising the active ingredient, which solid core is substantially covered with a film coating.

The compositions of the invention may comprise, for example, granules, tablets or capsules. Preferably the compositions of the invention will comprise tablets, most preferably compressed tablets.

There is provided in a preferred aspect of the invention a film coated tablet comprising a tablet core containing an effective amount of 3-[2-(dimethylamino) ethyl]-N-methyl-1H-indole-5-methanesulphonamide or a pharmaceutically acceptable salt or solvate thereof as active ingredient and a film coat on the tablet core.

We have found that the unpleasant taste associated with oral administration of the compound of formula (I) is substantially eliminated by the formulations of the present invention. The film coating also makes the formulations easier to handle and reduces potentially hazardous dust formation occurring during the packaging or administration of the drug. Surprisingly these advantages are attained without any significant loss in the bioavailability of the compound of formula (I) when compared to aqueous solutions or dispersible tablet formulations for oral administration to migraineurs Film-coated tablets according to the invention are therefore surprisingly effective in the treatment of migraine.

It is preferred that 3-[2-(dimethylamino)ethyl)]-N-methyl-1H-indole-5-methanesulphonamide should be employed in the compositions of the invention in the form of a physiologically acceptable salt. Such salts include salts of inorganic or organic acids such as hydrochloride, hydrobromide, sulphate, nitrate, phosphate, formate, mesylate, citrate, benzoate, fumarate, maleate, tartrate and succinate salts. Most preferably 3-[2-(dimethylamino)ethyl]-N-methyl-1H-indole-5-methanesulphonamide will be employed in the compositions of the invention in the form of its succinate (1:1) salt.

The film coating comprises a polymer. Suitable polymers include cellulose ethers, for example, hydroxypropyl methylcellulose, hydroxypropyl cellulose or methylcellulose, and copolymers of methacrylic acid and methyl methacrylate.

Preferably the film coating will comprise hydroxypropylmethyl cellulose.

The total film coating solids are generally applied to the solid dosage form, for example the tablet core, in an amount of from 2 to 5% w/w, preferably from 3 to 4% w/w, based on the weight of the solid dosage form.

The film coating may additionally comprise any pharmaceutically acceptable colourants or opacifiers including water soluble dyes, aluminium lakes of water soluble dyes and inorganic pigments such as titanium dioxide and iron oxide. Suitable colourants or opacifiers may comprise from 5% to 65% w/w, preferably from 25 to 50% w/w, based on the dry weight of film coating.

The film coating may also contain one or more plasticizing agents conventionally used in polymeric film coatings, for example polyethylene glycol, propylene glycol, dibutyl sebecate, mineral oil, sesame oil, diethyl phthalate and triacetin. Suitable plasticizing agents may comprise 1 to 40% preferably 5 to 20% w/w based on the dry weight of the film coating.

In addition to the compound of formula (I) or a physiologically acceptable salt or solvate thereof, compositions of the invention will preferably comprise pharmaceutically acceptable carriers and excipients, such as binding agents (e.g. pregelatinised maize starch, polvvinylpyrrolidone or hydroxypropylmethylcellulose); fillers (e.g. lactose, sucrose, mannitol, maize starch, microcrystalline cellulose or calcium hydrogen phosphate); lubricants (e.g. stearic acid, polyethylene glycol, magnesium stearate, talc or silica); disintegrants (e.g. potato starch, sodium starch glycollate or croscarmellose sodium); or wetting agents (e.g. sodium lauryl sulphate).

For the preparation of compositions according to the invention 3-[2-dimethylamino) ethyl]-N-methyl-1H-indole-5-methanesulphonamide or a physiologically acceptable salt or solvate thereof may be blended with suitable excipients and, if desired, granulated. Preferably 3-[2-(dimethylamino) ethyl]-N-methyl-1H-indole-5-methanesulphonamide will be granulated with a filler before admixture with the other excipients. Most preferably the filler employed will be lactose. Tablets in uncoated form may be prepared, for example, by compression of the powder blend or granulate, using a lubricant as an aid to tabletting. Compressed tablets are preferred.

The solid dosage form is then film-coated using a suspension comprising a suitable polymer in a suitable solvent. The preferred solvent for the film coating components is purified water but various classes of organic solvents commonly used in this art such as alcohols, ketones, ethers and chlorinated hydrocarbons, for example ethanol, acetone, methylene chloride and the like, may also be used. The solvent does not appear in the final product. The amount of solvent may be varied according to the equipment and coating conditions used to produce an aesthetically coated tablet.

The amount of 3-[2-(dimethylamino)ethyl]-N-methyl-1H-indole-5-methanesulphonamide, preferably in the form of a physiologically acceptable salt, employed in the compositions of the invention will preferably be in the range of about 25 mg to about 200 mg, most preferably about 50 mg or 100 mg, expressed as the weight of free base.

A further aspect of the invention provides a method of treating a mammal, including man, suffering from or susceptible to conditions associated with cephalic pain such as cluster headache, chronic paroxysmal hemicrania, headache associated with vascular disordersm, headache associated with substances or their withdrawal (for example drug withdrawal), tension headache and in particular migraine which comprises oral administration of a pharmaceutical composition comprising a film-coated solid dosage form of 3-[2-dimethylamino)ethyl]-N-methyl-1H-indole-5-methanesulphonamide or a pharmaceutically acceptable salt or solvate thereof as active ingredient. It will be appreciated that reference to treatment is intended to include prophylaxis as well as the alleviation of established symptoms.

It will be appreciated that the precise therapeutic dose of the active ingredient will depend on the age and condition of the patient and the nature of the condition to be treated and will be at the ultimate discretion of the attendant physician.

However, in general effective doses for the treatment of conditions associated with cephalic pain, for example acute treatment of migraine, will lie in the range of 10 to 500 mg, preferably 20 to 300 mg, most preferably 25 to 200 mg, for example 50 mg or 100 mg of the active ingredient per unit dose which could be administered in single or divided doses, for example, 1 to 4 times per day.

The invention is further illustrated by the following non-limiting examples wherein the active ingredient is 3-[2-(dimethylamino)ethyl]-N-methyl-1H-indole-5-methanesulphohamide (1:1) succinate.

EXAMPLE 1

| Tablet cores | Unit formula (mg/tablet) |
| --- | --- |
| Active ingredient/lactose granule* | 280.0 |
| Microcrystalline Cellulose Ph Eur | 15.5 |
| Croscarmellose Sodium USNF | 3.0 |
| Magnesium Stearate Ph Eur | 1.25–1.75 |
| Compound of formula (I) succinate | 140.0** |
| Lactose Ph Eur 170 mesh | 140.0 |

-continued

| Purified water Ph Eur | qs+ |
| --- | --- |

| Coating Suspension | % w/w |
| --- | --- |
| Hydroxypropyl methylcellulose Ph Eur | 10.0 |
| Opaspray white# | 5.0 |
| Purified Water Ph Eur to | 100.0++ |

*Active ingredient/lactose granule
+The water does not appear in the final product. Typical range 100–140 g per kg of blend
**Equivalent to 100 mg free base
++The water does not appear in the final product. The maximun theoretical weight of solids applied during coating is 11 mg/tablet.
Opaspray white is a proprietory film coating suspension, obtainable from Colorcon Ltd, UK, which contains hydroxypropyl methylcellulose and titanium dioxide.

The active ingredient and lactose were mixed together and granulated by the addition of purified water. The granules obtained after mixing were dried and passed through a screen, and the resulting granules were then mixed with the other tablet core excipients. The mix was compressed into tablets. The tablets were then film coated using the coating suspension in conventional film coating equipment.

EXAMPLE 2

The tablet cores were prepared as described in Example 1. The tablets were then film coated using the coating suspension given below and conventional film coating equipment.

| Coating Suspension | % w/w |
| --- | --- |
| Opadry pink## | 5.3 |
| Purified water Ph. Eur. to | 100.0++ |

++The water does not appear in the final product. The maximum theoretical weight of solids applied during coating is 9 mg/tablet.
Opadry pink is a proprietary film coating material, obtainable from Colorcon Ltd, UK which contains hydroxypropyl methylcellulose, titanium dioxide, red iron oxide and triacetin.

We claim:

1. A pharmaceutical composition for oral administration comprising a compressed film-coated tablet comprising a tablet core containing 25 to 200 mg of 3-[2-(dimethylamino) ethyl]-N-methyl-1H-indole-5-methanesulphonamide succinate (1:1) salt as active ingredient, and a pharmaceutically acceptable carrier or excipient and a film coating on said table core wherein the film coating is applied to the tablet core in an amount of from 2 to 5% w/w of the tablet.

2. A pharmaceutical composition as claimed in claim 1 in the form of a compression tablet.

3. A pharmaceutical composition as claimed in claim 1 wherein the film coating comprises a polymer.

4. A pharmaceutical composition as claimed in claim 3 wherein the polymer is hydroxypropyl methylcellulose.

5. A pharmaceutical composition as claimed in claim 1 wherein the composition comprises 50 to 100 mg of active ingredient.

6. A method of treating a man suffering from migraine which comprises administering the composition of claim 1 to the man.

* * * * *

Dedication

5,863,559 — Anthony John Phillips, Ware, Great Britain; Ian Keith Winterborn, Mississauga, Canada; John Malcolm Padfield, Uxbridge, Great Britain. ORAL DOSAGE FORM FOR TREATING MIGRAINE. Patent dated January 26, 1999. Disclaimer and dedication filed August 16, 2004, by the assignee, Glaxo Group, Ltd., d/b/a GlaxoSmithKline.

Hereby dedicates to the Public, claims 1, 2, 3, 4, 5, and 6 for the entire term of said patent.

*(Official Gazette, November 2, 2004)*